Nov. 8, 1949. H. C. SWIM Plant Pat. 895
ROSE PLANT
Filed April 6, 1948
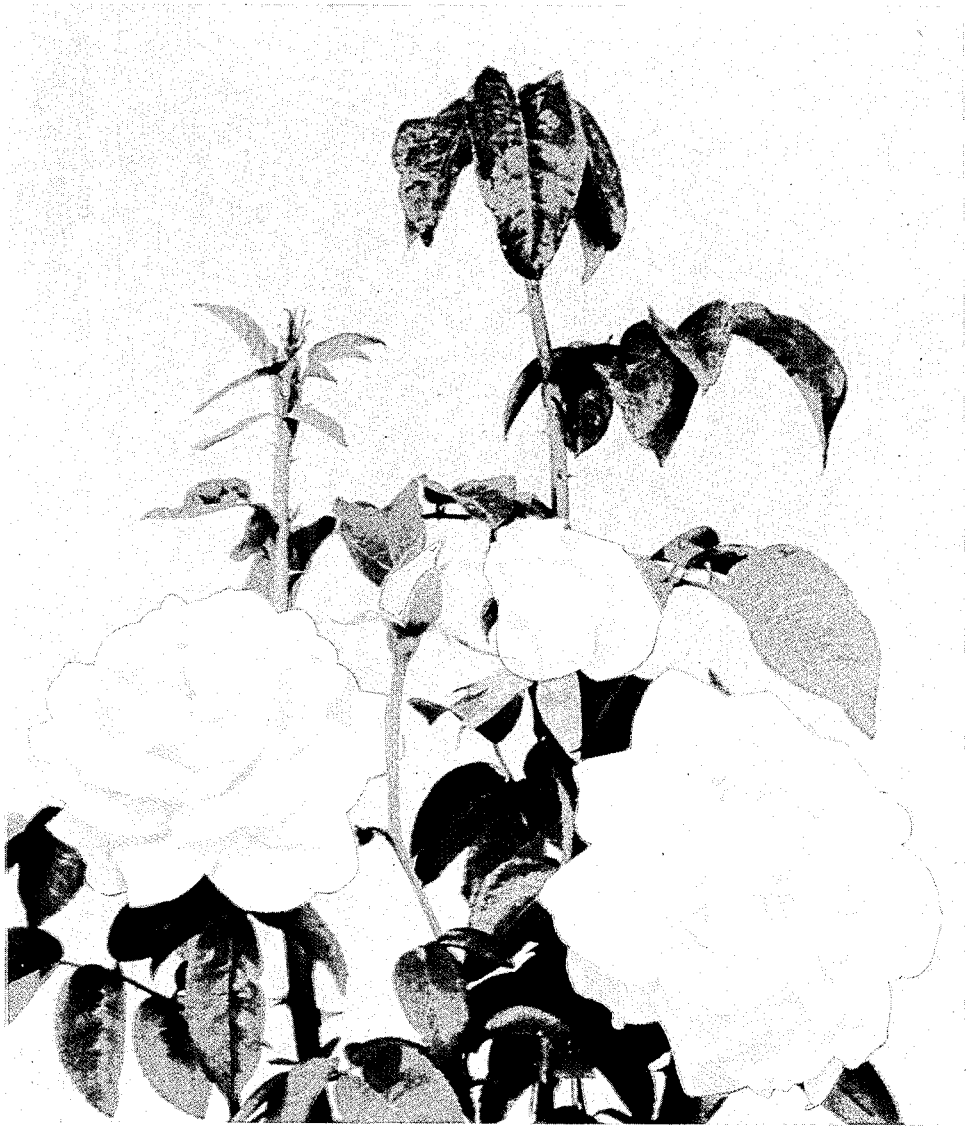
Inventor
H. C. Swim
By Robb & Robb
Attorneys Patented Nov. 8, 1949

Plant Pat. 895

UNITED STATES PATENT OFFICE

895

ROSE PLANT

Herbert C. Swim, Ontario, Calif., assignor to Armstrong Nurseries, Inc., Ontario, Calif., a corporation of California Application April 6, 1948, Serial No. 19,187

1 Claim. (Cl. 47—61)

The present invention relates to a new and distinct variety of rose plant resulting from a cross of two well known rose varieties, "Duquesa de Peñaranda" as the seed parent, and "Charlotte Armstrong" as the pollen parent.

This new variety possesses the following combination of distinctive characteristics:

(1) A new color in hybrid tea roses substantially as described and illustrated herein.

(2) A distinctive foliage unusual for its combination of large size, leathery-glossy texture and appearance and its typically bright shade of green color.

(3) A tendency in the flower to fade uniformly with a minimum of objectionable blue coloring under heat and bright sunlight.

(4) A flower unique in its neatness and balance throughout its life cycle.

(5) A plant moderate in growth producing heavy, short to medium length, stems and tending to continuity in production of flowers.

This new variety differs from its seed parent as follows:

(1) The new variety has flowers in the pink range whereas its seed parent variety produces a flower in orange tones.

(2) This new variety produces flowers that are exceptional for their balance in all stages whereas the variety of the seed parent produces flowers typically opening lopsided in shape.

(3) This new variety has approximately 50 per cent more petals than its seed parent.

This new variety may be distinguished from its pollen parent in the following manner:

(1) This new variety has a plant that is moderate in growth and tending to be stocky whereas "Charlotte Armstrong" has a plant that is rangy and tall.

(2) The color of the flower of this new variety is in the pink range whereas the flowers of "Charlotte Armstrong" are described as Spectrum Red to Blood Red.

(3) The foliage of this new variety is glossy, very large and with somewhat rugose surface whereas that of "Charlotte Armstrong" is merely large, dull surfaced and smooth.

(4) The foliage of this new variety is a bright shade of green whereas the foliage of "Charlotte Armstrong" tends more to the color that might be properly described as gray-green.

In the accompanying illustration are shown, specimens of the foliage and flowers at different stages of development.

Asexual reproduction shows that these characteristics hold true through succeeding propagations.

The following is a detailed description of the new variety, all references to color being in accordance with the R. F. Wilson's Horticultural Colour Chart, except where indicated to be in accordance with Ridgway's Color Standards and Nomenclature:

Type: Bush; outdoor; seedling; for cut flowers and garden decoration.

Class: Hybrid tea.

Breeding: Seedling.

*Seed parent.*—"Duquesa de Peñaranda" (unpatented).

*Pollen parent.*—"Charlotte Armstrong" (Plant Patent No. 455).

Propagation: Holds its distinguishing characteristics through succeeding propagations by budding.

*Flower*

Locality where grown: Ontario, California.

Flowers borne: Singly, occasionally two to four to stem in irregular cluster; on normal, short to medium length stems.

Quantity of bloom: Free; outdoors.

Continuity: Continuous during growing season.

Fragrance: Slight to moderate; spicy.

Bud:

*Peduncle.*—Medium length; medium to heavy; erect; moderately rough; few prickles; numerous gland-tipped cilia. *Color*—Absinthe Green, Plate XXXI (Ridgway), becoming near Mineral Red, Plate XXVII (Ridgway) on side exposed to sun.

*Before calyx breaks.*—*Size*—medium. *Form*—short; pointed to ovoid; with foliaceous appendages, tomentum, on the surface of the bud; with slender, entire, much cut foliaceous parts extending beyond the tip of the bud equal to ½ of its length.

*As calyx breaks.*—Color—near Cardinal Red, Plate 822/3, page 168. *Sepals*—inner surface—with fine, woolly tomentum. Margins covered by adjacent sepals are lined with tomentum, margins not covered by adjacent sepals are lined with tomentum and stipitate glands.

*As first petal opens.*—*Size*—medium to large. *Form*—medium length; pointed to ovoid. *Color*—outside: Rose Madder, Plate 23/1, page 23, with a spot of Lemon Yellow, Plate 4/2, page 4, at base of petal; inside: near Rose Madder, Plate 23, page 23, with a spot of Buttercup Yellow, Plate 5/2, page 5, at base of petal. Petal with a narrow margin of Rose Madder, Plate 23/3, page 23.

*Opening.*—Opens up well.

Bloom: Size, when fully open—medium to large; 3½ inches to 4½ inches.

*Petalage.*—Double; from 20 to 30 petals; arranged regularly; 5 to 15 petaloids arranged irregularly.

*Form.*—Open to slightly cupped, high center at first; becoming open; petals remaining at first very loosely rolled outward; becoming later, at maturity, loosely rolled outward.

Petals: Thick; with inside velvety and outside satiny.

*Shape.*—Outside: round; scalloped with one to two notches. Intermediate: obovate; scalloped with one to two notches. Inside: obovate; scalloped with one to two notches.

*Color.*—Colors may be modified by being margined, shaded or washed with other colors.

This description of a newly opened flower was made from a rose grown outdoors in the month of November, at Ontario, California:

*Color.*—*Outside petal*—outside surface: near Rose Madder, Plate 23/2, page 23, shading to Rose Madder, Plate 23/3, page 23, with a small spot of Aureolin, Plate 3/2, page 3, at base of petal; inside surface: near Rose Madder, Plate 23/1, page 23, with a narrow margin of Rose Madder, Plate 23/3, page 23, with a spot of Lemon Yellow, Plate 4/2, page 4, at base of petal. *Intermediate petal*—Outside surface: near Neyron Rose, Plate 623/2, page 76, with a spot of Aureolin, Plate 3/2, page 3 at base of petal; inside surface: near Rose Madder, Plate 23/2, page 23, with a narrow margin of Rose Madder, Plate 23/3, page 23, with a spot of Lemon Yellow, Plate 4/2, page 4, at base of petal. *Inner petal*—outside surface: near Neyron Rose, Plate 623/2, page 76, shading to Camellia Rose, Plate 622/1, page 148, with a spot of Aureolin, Plate 3/1, page 3, at base of petal; inside surface: near Rose Madder, Plate 23/2, page 23, with a narrow margin of Rose Madder, Plate 23/3, page 23, becoming washed near base with Geranium Lake, Plate 20/2, page 20, with a spot of Lemon Yellow, Plate 4/1, page 4, at base of petal.

This description was made from a rose that was open for three days indoors in the month of November, at Ontario, California:

*Color.*—*Outside petal*—outside surface: Rhodamine Pink, Plate 527/2, page 138, with a narrow margin at edge of petal of white with a very small spot of Aureolin, Plate 3/2, page 3, at base of petal; inside surface: Rhodamine Pink, Plate 527/1, page 138, with a narrow margin at edge of petal of white with a small spot of Aureolin, Plate 3/2, page 3, at base of petal. *Inside petal*—Outside surface: Rhodamine Pink, Plate 527/2, page 138, with a narrow margin of white at edge of petal with a small spot of Aureolin, Plate 3/2, page 3, at base of petal; inside surface: Rhodamine Pink, Plate 527/1, page 138, with a narrow margin of white at edge of petal with a small spot of Aureolin, Plate 3/2, page 3, at base of petal.

*General color effect.*—Newly opened flower—near Rose Madder, Plate 23/2, page 23. Three days open—near Rhodamine Pink, Plate 527/1, page 138.

*Behavior.*—Drop off cleanly; affected by hot, dry weather, becoming much lighter in shade.

*Flower longevity.*—On bush in garden—three to four days in November. Cut roses grown outdoors kept at living room temperatures—two to three days in November.

*Reproductive organs*

Stamens: Many, approximately 100 in number; arranged regularly about pistils.

Filaments: Medium to long; 5 to 15 mm. in length; most with anthers. *Color*—near Mandarin Red, Plate 17/2, page 17, shading through Cadmium Orange, Plate 8/1, page 8, to Indian Yellow, Plate 6/2, page 6, at apex.

Anthers: Medium size; all open at once. *Color*—near Indian Yellow, Plate 6/3, page 6, becoming Indian Yellow, Plate 6/2, page 6, at margins.

Pollen: Moderate to abundant. *Color*—Yellow Ochre, Plate o7/1, page 101.

Pistils: Medium to many; approximately 50 in number.

Styles: Uneven; short to medium; 4 to 9 mm. in length; thin; loosely bunched. *Color*—near Uranium Green, Plate 63/3, page 63, at base becoming near Carmine, Plate 21, page 21, at apex.

Stigma: Translucent but near Aureolin, Plate 3/3, page 3.

Ovaries: All enclosed in calyx.

Sepals: Permanent; moderately long; curled. *Color*—inside: near Buffy Brown, Plate XL (Ridgway); outside: near Buffy Brown, Plate XL (Ridgway).

*Plant*

Foliage:

*Leaves.*—Compound of five to seven leaflets; moderately abundant; very large; leathery; semi-glossy; wrinkled.

*Leaflets.*—Shape—ovate lanceolate; with apex acute; base cordate; margin doubly serrate.

*Color.*—*Mature*—upper surface: Yew Green, Plate XXXI (Ridgway); under surface: Asphodel Green, Plate XLI (Ridgway). *Young*—upper surface: near Absinthe Green, Plate XXXI (Ridgway), washed with near Garnet Brown, Plate I (Ridgway); under surface: near Deep Chrysolite Green, Plate XXXI (Ridgway), washed with Mineral Red, Plate XXVII (Ridgway).

*Rachis.*—Heavy. Upper side—grooved, glandular. Under side—prickly.

*Stipules.*—Medium to long; moderately wide; with moderately short points, turning out at an angle of more than 45°.

*Disease.*—Resistant to mildew.

Growth:

*Habit.*—Bushy; upright; much branched.

*Growth.*—Moderate.

*Canes.*—Medium to heavy.

*Main stems.*—Near Light Cress Green, Plate XXXI (Ridgway) becoming washed with Verona Brown, Plate XXIX (Ridgway), on side exposed to sun. *Large prickles*—several; medium length; hooked downward; with short, broad base. Color—near Snuff Brown, Plate XXIX (Ridgway). *Small*

*prickles*—few. Color—near Snuff Brown, Plate XXIX (Ridgway). *Hairs*—none.

*Branches.*—Near Light Cress Green, Plate XXXI (Ridgway). *Large prickles*—several; short to medium; hooked downward; with short, broad base. Color—near Rood's Brown, Plate XXVIII (Ridgway). *Small prickles*—several. Color—near Rood's Brown, Plate XXVIII (Ridgway). *Hairs*—none.

*New shoots.*—Absinthe Green, Plate XXXI (Ridgway) washed with Garnet Brown, Plate I (Ridgway). *Large prickles*—several; medium length; hooked downward; with short, narrow base. Color—near Garnet Brown, Plate I (Ridgway). *Small prickles*—few. Color—near Garnet Brown, Plate I (Ridgway). *Hairs*—none.

I claim:

A new and distinct variety of rose plant characterized as to novelty by its habit of moderate growth and production of heavy, short to medium length stems with a tendency to continuity in production of flowers; by its large size foliage of leathery, glossy texture and appearance and typically bright green shade; by the color of its flowers, new in hybrid teas, and unique in neatness and balance throughout their life cycle; and by the tendency of the flowers to fade uniformly with a minimum of objectionable blue coloring under heat and sunlight, substantially as shown and described.

HERBERT C. SWIM.

No references cited.